United States Patent
Jones

(10) Patent No.: US 9,814,904 B2
(45) Date of Patent: Nov. 14, 2017

(54) SKIN TREATMENT APPARATUS

(71) Applicant: CYDEN LIMITED, Swansea, South Wales (GB)

(72) Inventor: Stuart Terry Jones, Swansea (GB)

(73) Assignee: Cyden Limited, Swansea (GB)

( * ) Notice: Subject to any disclaimer, the term of this patent is extended or adjusted under 35 U.S.C. 154(b) by 707 days.

(21) Appl. No.: 14/360,703

(22) PCT Filed: Nov. 23, 2012

(86) PCT No.: PCT/GB2012/052912
§ 371 (c)(1),
(2) Date: May 27, 2014

(87) PCT Pub. No.: WO2013/076508
PCT Pub. Date: May 30, 2013

(65) Prior Publication Data
US 2014/0324135 A1 Oct. 30, 2014

(30) Foreign Application Priority Data

Nov. 25, 2011 (GB) .................... 1120381.7

(51) Int. Cl.
*A61N 5/06* (2006.01)
*A61B 18/18* (2006.01)
(Continued)

(52) U.S. Cl.
CPC .......... *A61N 5/0616* (2013.01); *A61B 18/203* (2013.01); *A61B 2018/00452* (2013.01);
(Continued)

(58) Field of Classification Search
None
See application file for complete search history.

(56) References Cited

U.S. PATENT DOCUMENTS 4,580,557 A * 4/1986 Hertzmann ............ A61B 18/20
219/121.61
6,267,723 B1 * 7/2001 Matsumura .......... A61B 5/0002
128/903
(Continued)

FOREIGN PATENT DOCUMENTS

| DE | 199 54 710 C1 | 3/2001 |
| EP | 1 166 723 A2 | 1/2002 |
| WO | 00/53261 A1 | 9/2000 |

OTHER PUBLICATIONS iPulse, SmoothSkin Plus, Intense Pulsed Light Permanent Hair Reduction, Instructions for Use, Mar. 2011.*
(Continued)

*Primary Examiner* — Lynsey Eiseman
*Assistant Examiner* — Manolis Pahakis
(74) *Attorney, Agent, or Firm* — Kohn & Associates, PLLC; Kenneth Kohn

(57) ABSTRACT

The apparatus includes a source of treatment radiation which is arranged to generate radiation at one of a plurality of radiation parameters (such as power levels), a control unit and a base unit. The control unit is arranged to removably dock with the base unit and includes a sensor which can sense one of a plurality of skin parameters, and an actuator for enabling a user to interface with the control unit. The control unit operates in a sensing mode, in which the control unit is undocked from the base unit to sense a parameter of skin to be treated (such as skin tone), and a control mode in which the control unit is docked to the docking unit and is arranged to select the power level of the radiation generated by the source.

8 Claims, 4 Drawing Sheets

(51) Int. Cl.
*A61B 18/20* (2006.01)
*A61B 18/00* (2006.01)

(52) U.S. Cl.
CPC ............... *A61B 2018/00642* (2013.01); *A61B 2018/00702* (2013.01); *A61B 2018/00726* (2013.01); *A61B 2018/00732* (2013.01); *A61B 2018/00785* (2013.01); *A61B 2560/0456* (2013.01); *A61N 2005/0626* (2013.01); *A61N 2005/0644* (2013.01)

(56) References Cited

U.S. PATENT DOCUMENTS

| | | | | |
|---|---|---|---|---|
| 6,603,995 | B1* | 8/2003 | Carter | A61B 5/0404 600/509 |
| 6,716,219 | B1* | 4/2004 | Koch | A61F 9/00736 422/300 |
| 6,736,832 | B2* | 5/2004 | Lenderink | A61B 5/0066 128/898 |
| 6,758,845 | B1* | 7/2004 | Weckwerth | A61B 18/203 128/898 |
| 6,790,178 | B1* | 9/2004 | Mault | A61B 5/0011 128/903 |
| 8,149,108 | B2* | 4/2012 | Hamel | A61B 1/00006 340/10.1 |
| D660,974 | S * | 5/2012 | Jones | D24/209 |
| D666,290 | S * | 8/2012 | Jones | D24/133 |
| 8,647,287 | B2* | 2/2014 | Greenberg | A61B 5/002 600/595 |
| 2002/0049432 | A1* | 4/2002 | Mukai | A61B 18/203 606/9 |
| 2004/0073095 | A1* | 4/2004 | Causey, III | A61B 5/0002 600/300 |
| 2004/0260210 | A1* | 12/2004 | Ella | A61H 7/008 601/7 |
| 2005/0085875 | A1* | 4/2005 | Van Zuylen | A61N 5/0616 607/88 |
| 2006/0197660 | A1* | 9/2006 | Luebke | G08B 25/009 340/539.26 |
| 2007/0255114 | A1* | 11/2007 | Ackermann | G06F 8/65 600/300 |
| 2007/0265645 | A1* | 11/2007 | Birk | A61B 5/0031 606/157 |
| 2008/0048028 | A1* | 2/2008 | Walneck | A61N 5/0616 235/381 |
| 2008/0108884 | A1* | 5/2008 | Kiani | A61B 5/0002 600/301 |
| 2009/0005651 | A1* | 1/2009 | Ward | A61B 5/00 600/300 |
| 2009/0306639 | A1* | 12/2009 | Nevo | A61B 18/02 606/21 |
| 2010/0076348 | A1* | 3/2010 | McNames | A61B 5/4082 600/595 |
| 2010/0145236 | A1* | 6/2010 | Greenberg | A61B 5/1101 600/595 |
| 2010/0211713 | A1* | 8/2010 | Waldhoff | A61B 5/0002 710/303 |
| 2010/0324611 | A1* | 12/2010 | Deming | A43B 3/0005 607/2 |
| 2012/0143291 | A1* | 6/2012 | Owens | A61B 18/203 607/90 |
| 2013/0144280 | A1* | 6/2013 | Eckhouse | A45D 26/00 606/9 |
| 2013/0197494 | A1* | 8/2013 | Koifman | A61B 18/203 606/17 |
| 2015/0230863 | A1* | 8/2015 | Youngquist | A61B 18/203 606/9 |

OTHER PUBLICATIONS

Laser Therapeutics Inc., The Healing Power and Energy of Light, Oct. 18, 2009, retrieved from http://www/lasersmokecessation.com/medicom_laser.htm with the Wayback Machine.*

* cited by examiner

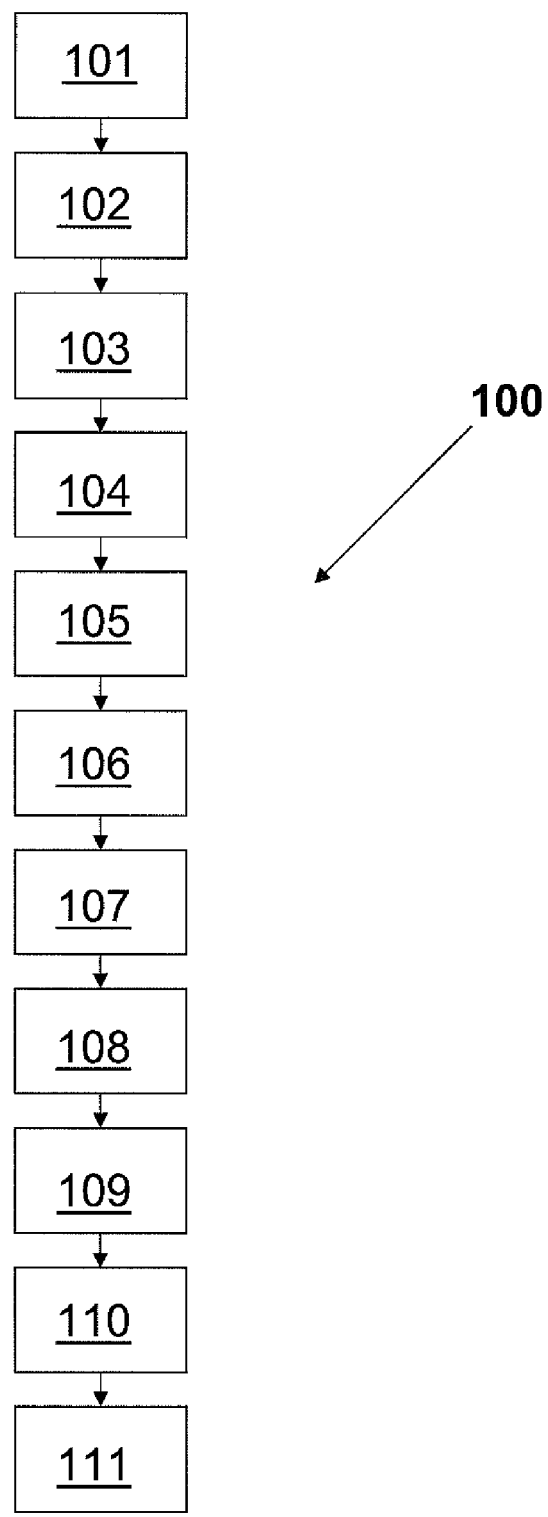

SKIN TREATMENT APPARATUS

BACKGROUND OF THE INVENTION

1. Technical Field

The present invention relates to a skin treatment apparatus, and methods of use thereof.

2. Background Art

It is known to treat skin (for example, for cosmetic purposes such as depilation, minimisation of skin blemishes or skin rejuvenation, as well as for dermatological treatment of skin conditions such as acne or rosacea) by exposing the skin to controlled dosages of optical radiation, such as high intensity broadband light pulses. This procedure generally involves radiation spanning substantially the entire visible spectrum, using dosages determined by a combination of energy intensity and pulse duration.

Apparatus used to treat skin using IPL (intense pulsed light) is now increasingly available for use by the general public, with the result that there is a requirement to avoid misuse of such apparatus through misunderstanding or abuse.

Applicants have now devised an improved skin treatment apparatus.

SUMMARY OF THE INVENTION

The present invention provides for a skin treatment apparatus, including:

(a) a source of skin treatment radiation which is configured to generate radiation having at least one variable radiation parameter, (b) a control unit for controlling a magnitude of the at least one variable radiation parameter, (c) a base unit to which the control unit can be selectively either docked or undocked, the control unit being removable when undocked, (d) a sensor for sensing a measurable skin parameter, and (e) an actuator for enabling a user to interface with the control unit, the control unit being configured to operate in respective sensing and control modes, wherein in the sensing mode the control unit is undocked from the base unit and the sensor can sense the measurable parameter of the skin, and wherein in the control mode said control unit is docked to the base unit and arranged to control operation of the source of skin treatment radiation in dependence of the sensed skin parameter.

DESCRIPTION OF THE DRAWINGS

Other advantages of the present invention are readily appreciated as the same becomes better understood by reference to the following detailed description when considered in connection with the accompanying drawings wherein.

DETAILED DESCRIPTION OF THE INVENTION

Figure 1:
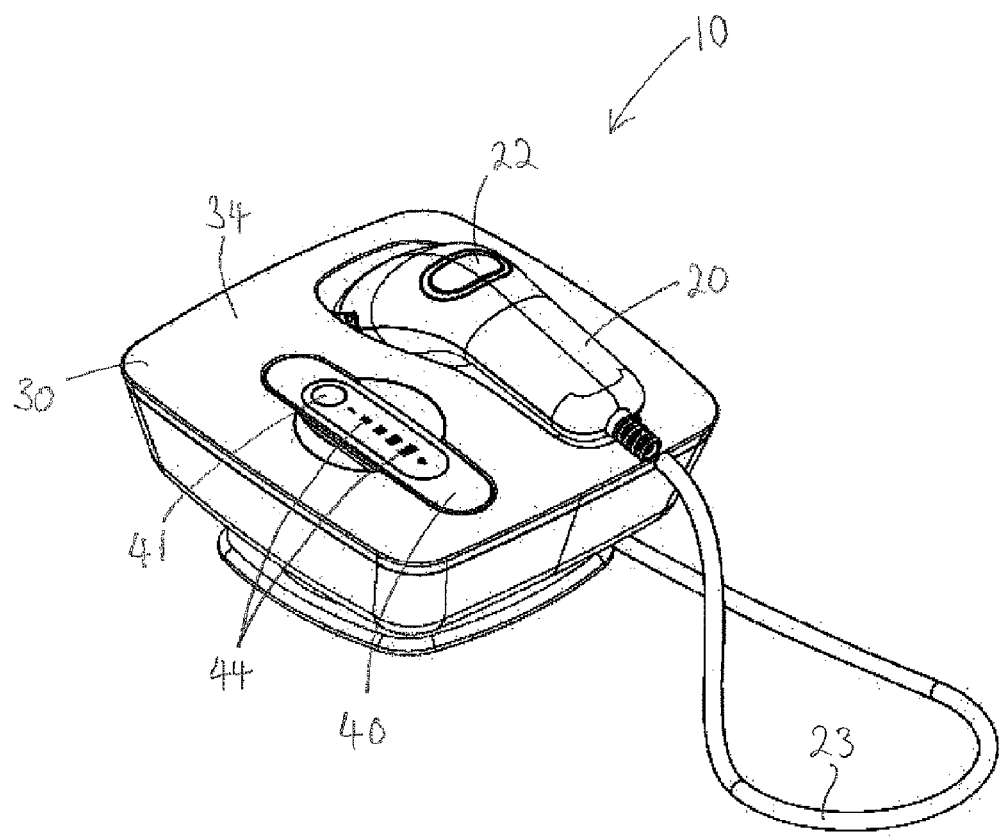
FIG. 1 is a schematic illustration of a skin treatment apparatus according to an embodiment of the present invention with the control unit docked to the base unit.
Figure 2:
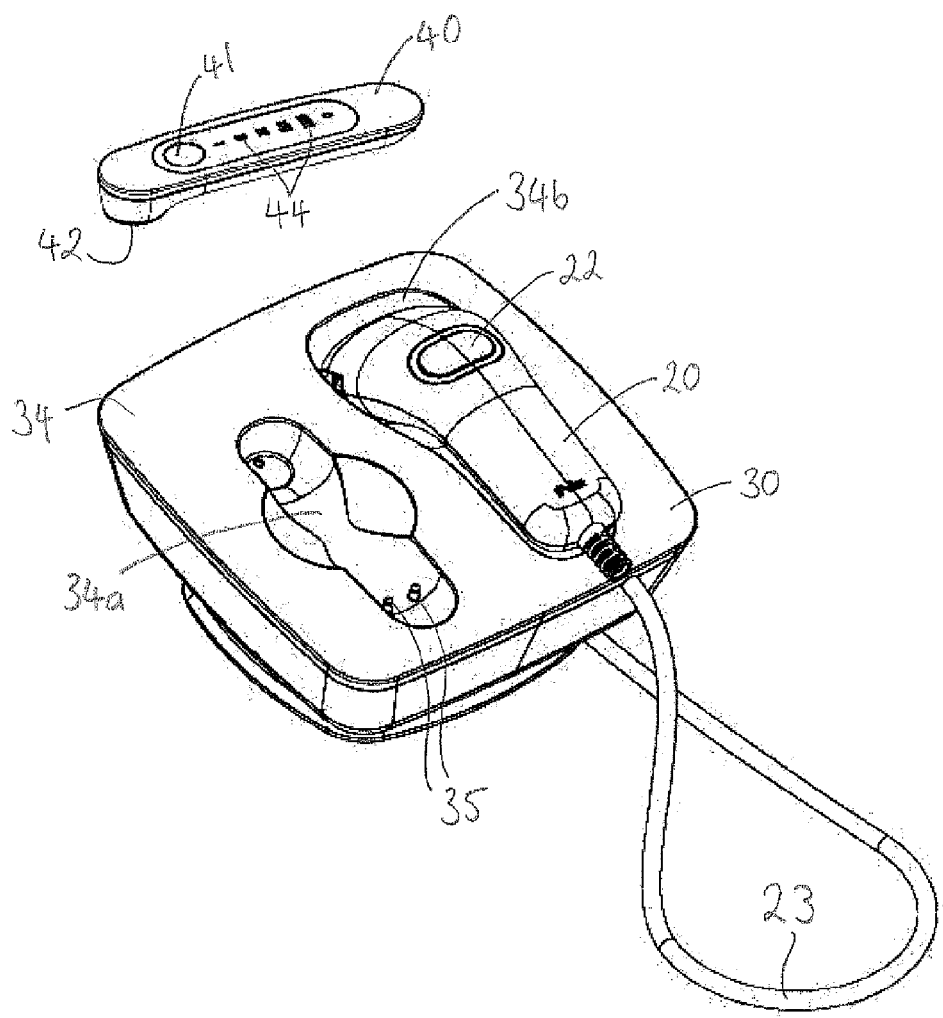
FIG. 2 is a schematic illustration of the skin treatment apparatus of FIG. 1, with the control unit removed from the base unit.
Figure 3:
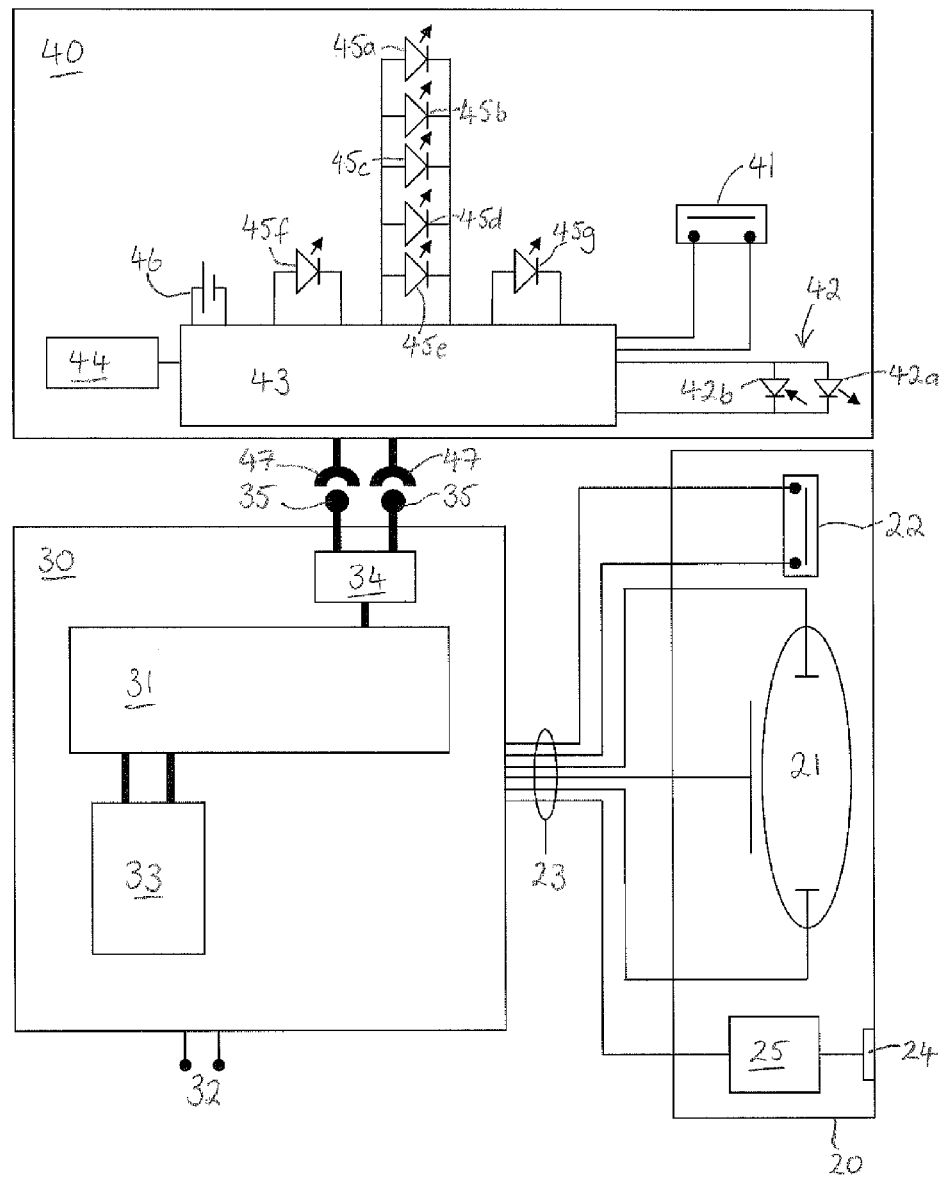
FIG. 3 is a schematic exemplary circuit diagram suitable for use in the skin treatment apparatus illustrated in FIG. 1; and, FIG. 4 is a schematic illustration of a method of operating skin treatment apparatus in a sequence of operations according to the invention.

Referring to FIGS. 1 to 3 of the drawings, there is illustrated skin treatment apparatus 10 according to an embodiment of the present invention for treating skin disorders and conditions, or for cosmetic purposes such as depilation. The apparatus 10 includes a source of treatment radiation, such as a discharge lamp 21, which is arranged to generate high intensity pulses of optical radiation. The lamp 21 is provided within a hand held illumination unit 20 so that the lamp 21 may be suitably positioned adjacent the desired area of skin to be treated. The hand held unit 20 further includes an actuator, such as a trigger 22, which may be pressed to activate the source and thus cause radiation to be emitted therefrom.

Preferably, the source of treatment radiation includes an optical source, such as a source of broadband radiation. The latter is sometimes referred to as an "intense pulsed light" (IPL) system, which operates over substantially over the entire visible spectrum (although sometimes it may be desirable to filter out part only of that broadband white light spectrum).

The source of treatment radiation is preferably provided within the hand held unit 20, which is removably coupled to a base unit 30 separately from a control unit 40. The source of radiation preferably includes a source of optical radiation, and is preferably removably located within the hand held unit 20.

The apparatus 10 further includes the base unit 30 and the control unit 40 which is arranged to removably dock with the base unit 30. The control unit 40 is arranged to operate in one of two distinct modes, depending on whether the control unit 40 is docked or undocked with the base unit 30. When undocked from the base unit 30, the control unit 40 is arranged to operate in a sensing mode and to determine a measurable parameter of the skin to be treated, such as a skin tone or colour, a skin depth, or a level of oiliness of the skin, for example. The measurable skin parameter being sensed is typically the degree of pigmentation (also known as skin tone), which may be categorised in a well known scale which ranges from 1 (for light skinned North European) to 6 (for very dark-skinned Afro-Caribbean). Alternatively, or in addition thereto, the measurable skin parameter may, for example, be a thickness of one or more layers of the skin, a measure of the skin's oiliness, or a parameter of blood in a skin layer. When docked with the base unit 30, the control unit 40 is arranged to operate in a control mode for controlling a variable parameter of the radiation to be generated from the source. It is envisaged, that the variable radiation parameter may comprise one or more of a power level of the radiation which is to be generated by the lamp 21, a duration for which the source generates radiation once activated, such as a pulse duration, or a frequency of applications per activation, for example. For the purposes of the following description, the radiation parameter is considered to be a radiation power level, however, the skilled reader will recognise that alternative and/or additional radiation parameters may be used.

Preferably, the control unit 40 is further arranged to select the magnitude of the radiation parameter when operating in the control mode. The control unit 40 may be arranged to inhibit operation of the source of radiation in the event that a sensed skin parameter falls outside a predetermined range and/or to limit the magnitude of the radiation parameter according to the sensed skin parameter. In an embodiment of the present invention, the control unit is preferably arranged to select a maximum permissible parameter of radiation, such as power, to be generated from the radiation source, in dependence of the sensed measurable skin parameter, such as skin tone.

Accordingly, the control unit may be advantageously used for both for the sensing of the skin parameter and for the selection of the magnitude of the radiation parameter, such as the radiation power, and therefore can be used to establish an ordered sequence of steps that a user must perform before treatment may be applied to skin. For example, the selection of the radiation power (that is, the output power) may be performed by appropriate selection of the electrical power input.

The control unit 40 includes an actuator, such as a button 41 for enabling a user to interface and thus operate the control unit 40, and a sensor 42 for sensing the measurable skin parameter, such as a tone or colour of the skin to be treated The skilled reader will recognise that alternative or additional skin parameter may be sensed. Preferably, the radiation source is arranged to generate radiation comprising a plurality of radiation parameter magnitudes, and the actuator is such that the radiation parameter magnitude can be selectably reduced from a predetermined maximum (as determined by the measured skin parameter), when a user actuates the actuator and the control unit 40 is docked (in the control mode). The actuator is preferably arranged such that when sequentially actuated in the control mode, it selects progressively lower parameter magnitudes. Once the lowest parameter magnitude has been selected, further actuation of the actuator preferably resets the parameter magnitude to a predetermined maximum. In this respect, a user is permitted to select a lower power level, for example, than that appropriate for a relevant skin tone, but is prevented from selecting a higher power level which might otherwise have led to an overexposure of the skin.

The sensor 42 includes a transmitter 42a, which is arranged to transmit sensing radiation through a window (not shown) of the control unit 40 onto the skin to be treated. The sensor 42 further includes a receiver 42b, such as a photodiode, which is arranged to receive radiation reflected from the skin surface. The intensity of the received radiation is found to be representative of the tone of the skin, for example a light skin tone will reflect more than a dark skin tone. The control unit 40 is arranged to process the intensity of the received radiation using a processor 43 provided therein, and to compare the intensity with a calibrated set of intensity measurements to determine the sensed skin tone (or skin parameter), which is then stored in a first memory 44 of the control unit 40.

Preferably, the base unit 30 includes a second memory and the sensed skin parameter is downloadable from the control unit 40 to the second memory when the control unit 40 is docked. In this manner, the base unit 30 can store the sensed parameter of the skin to be treated, and the stored parameter can be arranged to limit the magnitude of the radiation parameter, such as the power of radiation, which is generated by the radiation source (thus serving to minimise overexposure of the user's skin to radiation, for example). Alternatively, or in addition thereto, the stored parameter may be used to limit the duration of applied radiation, such as a pulse duration for example.

The control unit 40 further includes a graded screen or a plurality of indicators 45a-f, such as a series of individual lights, i.e. a plurality of light emitting diodes, the indicators being arranged to illuminate depending of the sensed skin tone and thereby to alert the user to the tone of skin sensed, and also a battery supply 46, such as a coin or disc battery, for powering the control unit 40 when undocked from the base unit 30. The plurality of indicators 45a-f can be used for indicating the selected magnitude of the radiation parameter, such as the power of radiation to be generated by the source. When individual lights are used, the particular number of the light in the sequence may be indicative of the relevant magnitude. When a graded screen is used, the colour on the screen may be used to indicate the relevant magnitude.

The base unit 30 includes a processor 31 for processing the information downloaded from the control unit 40, and the base unit 30 is powered from a mains supply 32. The base unit 30 further includes an electrical supply, such as a capacitor 33, which is charged from the mains supply 32 and is arranged to power the discharge lamp 21 via a power cable 23. In this respect, the hand held unit 20 and base unit 30 are coupled via the power cable 23.

The base unit 30 further includes a housing 34 having a recess 34a disposed therein for receiving the control unit 40. The recess 34a includes a pair of contact pins 35 which are arranged to contact a pair of contact pads 47 provided upon the control unit 40, when the latter is docked. The contact pins 35 and pads 47 provide for communication of the control unit 40 with the base unit 30 and further provide power for the control unit 40 when docked with the base unit 30.

The high voltages associated with the capacitor 33 of the base unit 30 are separated from the control unit 40 by an interface unit 34, which interfaces the contact pins 35 with the electronic circuitry of the base unit 30. The interface unit 34 may comprise a circuit breaking facility, such as a residual current detector, such that in the event that the base unit 30 develops a fault, for example, then the large voltages and currents developed by the capacitor can be isolated from the control unit 40.

The base unit 30 as shown includes a further recess 34b for receiving the hand held unit 20. Magnets (not shown) may be provided to hold the respective control unit 40 and hand held unit 20 each within its respective recess 34a, 34b.

Referring to FIG. 4 of the drawings, there is illustrated a method 100 of operating a dermatological treatment apparatus, such as the above described treatment apparatus 10, according to an embodiment of the present invention. In treating a skin disorder, or rejuvenating skin, for example, the apparatus 10 is first switched on at step 101 via a switch (not shown) and the control unit 40 is removed from the base unit 30 at step 102 to remove the apparatus 10 from a power conservation or standby mode. After removal from the base unit 30, the control unit 40 operates in a sensing mode and is powered by the battery supply 45. The window (not shown) of the control unit 40 is subsequently placed over the area of the skin to be treated at step 103 and the button 41 pressed to cause sensing radiation to be emitted from the transmitter 42a in order to determine the parameter of the skin to be treated at step 104. Once a measurement has been made, a respective light emitting diode 45a-e illuminates at step 105 to give an indication of the sensed skin parameter, for example, the sensed skin tone. If an apparently invalid skin tone is sensed, then a corresponding light emitting diode 45f will illuminate to inform the user that a further measurement is required. For example, in the event that the sensed radiation is indicative of a too light or too dark skin tone, then the control unit 40 will illuminate the respective light emitting diode 45f. In the event that the user subsequently docks the control 40 unit to the base unit 30, namely without first obtaining a valid skin tone, then the control unit 40 will prevent the lamp 21 from generating radiation.

Upon obtaining a valid measurement of the skin parameter, such as skin tone, the control unit 40 is then docked to the base unit 30 at step 106 and the sensed skin tone is downloaded to the base unit 30 (via the contact pins 35 and pads 47) at step 107. The download process is arranged to take place automatically upon docking the control unit 40, but, it is to be appreciated that the download may, if wished, be initiated by the user by pressing the button 41, for example. The control unit 40 subsequently enters a control mode, in which the control unit 40 controls the parameter, such as the power, of radiation to be generated by the lamp 21. Upon receiving the measured skin parameter from the control unit 40, the processor 31 of the base unit 30 initiates charging of the capacitor 33 at step 108 to a level necessary to generate a pre-determined power of radiation from the lamp 21, corresponding to that needed for the respective treatment of that particular skin tone.

If wished, a user may reduce the charge on the capacitor 33 at step 109 and thus the power of radiation to be generated from the lamp 21, to a power level corresponding to a different (lower or lighter) skin tone, by pressing the button 41 on the control unit 40. The apparatus is such that each depression of the button 41 further reduces the power level, namely the radiation parameter which is indicated to the user via indicators 45*a-e*, until the lowest parameter value is selected. Upon further depressing of the button 41, the control unit 40 is arranged to return the radiation parameter to that corresponding to the sensed skin parameter.

Once the desired power level has been selected, the user removes the hand held unit 20 from the base unit 30 and positions the lamp 21 adjacent the area of the skin to be treated at step 110. The hand held unit 20 further includes a sensor 24 arranged to sense contact of the hand held unit 20 with the skin to be treated and a processor 25 associated with the unit 20 permits the lamp 21 to emit radiation only when the hand held unit 20 contacts the skin. Accordingly, upon suitably positioning the unit 20 adjacent the skin to be treated, the user subsequently presses the trigger 22 at step 111 disposed thereon to cause radiation to be emitted to treat the skin. Further treatment radiation may then be applied to neighbouring areas of skin as required, by repositioning the hand held unit 20 and further pressing the trigger 22. However, if no further activation of the lamp 21 is made within a predetermined time period, for example 3 minutes, then a further skin tone reading will need to be made with the control unit 40 and the control unit 40 will then need to be re-docked to the base unit 30, before a further application of radiation can be made.

Similarly, if the radiation source is not activated within a pre-determined time period, for example 10 minutes, of docking the control unit 40 with the base unit 30 following a measurement of a valid skin tone, then a further skin tone measurement will need to be made before any application of radiation can be made. Thus in general, the apparatus preferably further includes a timer or timing circuit for preventing generation of radiation from the source in the event that the radiation source is not activated within a pre-determined time following the sensing of the skin parameter or docking of the control unit 40 with the base unit 30. The timer or timing circuit preferably also prevents subsequent generation of radiation after a further pre-determined time has elapsed following such activation.

In an alternative embodiment, it is envisaged that the control unit 40 may be arranged to sense the skin parameter in a sensing mode, and upon obtaining a valid measurement of the skin parameter and subsequently docking the unit 40 to the base unit 30, the control unit 40 is arranged to simply generate radiation from the lamp 21 comprising the radiation parameter which corresponds to the measured skin parameter. In this embodiment, the control unit 40 is arranged to simply enable or disable (in the event that an invalid skin tone is measurement is obtained) the firing of the radiation from the lamp 21, rather than also enabling a user specified reduction in the power level.

It is envisaged that the lamp 21 used to generate the radiation, may be disposed within a cartridge (not shown) which may be removably coupled within the hand held unit 20. Accordingly, once the discharge lamp 21 has reached the end of its useful life, the cartridge (not shown) and thus the lamp 21, may be readily replaced. In this respect, the control unit 30 further includes an indicator 45*g* to alert the user of the number of applications remaining before the cartridge (not shown) requires replacing.

The present invention further provides a method of operating skin treatment apparatus according to the invention by removing the control unit from the base unit, using the sensor provided in the control unit to sense the measurable parameter of skin to be treated, docking the control unit to the base unit, and, controlling operation of the source of skin treatment radiation in dependence of the sensed skin parameter.

The method preferably further includes using the control unit to select a magnitude of the variable parameter of radiation to be generated from the source.

In an embodiment of the present invention, the method further includes limiting the maximum power level of the radiation to be generated by the source, depending on the sensed skin parameter. The method preferably further includes selectively reducing the power of the radiation to be generated by the radiation source to a level below the maximum level.

The method preferably further includes activating the radiation source to generate radiation therefrom. Preferably, the method further includes preventing radiation from being generated from the source in the event that the radiation source is not activated within a pre-determined time following the sensing of the measurable skin parameter or docking of the control unit with the base unit.

After any initial activation of the radiation source, then it is preferred to positively prevent further activation if the source is not activated within a pre-determined time from the initial activation.

The present invention further provides a skin treatment procedure, which includes carrying out the method according to the invention and using the radiation source in the apparatus to treat skin, typically for cosmetic purposes.

Specifically, the skin treatment may be for the purposes of depilation, for other cosmetic purposes such as treatment of birth marks or rejuvenation of collagen, or for such medical purposes as treatment of acne, rosacea or the like.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A skin treatment apparatus, said apparatus comprising:
   a handpiece with a source of skin treatment radiation configured to generate intense pulsed light radiation;
   a control unit for controlling a variable radiation parameter of said intense pulsed light radiation generated from said source, wherein the variable radiation parameter includes one or more of a power, a pulse duration or a pulse frequency per activation, wherein the control unit is part of a separate handheld unit than the handpiece;
   a base unit including a processor, the base unit having cradles configured to enable docking and undocking of the handpiece and the control unit therein;
   a sensor on said control unit for sensing a skin parameter, wherein the skin parameter includes one or more of a skin tone, a skin layer thickness, a level of oiliness, or a skin blood parameter; and
   an actuator for enabling a user to interface with said control unit;
   wherein said control unit is configured to operate in a sensing mode when said control unit is undocked from said base unit, and, in the sensing mode:
      said sensor is configured to sense the skin parameter, and
   wherein said control unit is configured to operate in a control mode when said control unit is docked to said base unit, and, in the control mode:
      said control unit automatically transfers the skin parameter sensed by the sensor in the sensing mode to the processor of the base unit and selects a skin safety limit for the variable radiation parameter based on the sensed skin parameter;
      said processor initiates the source to charge at the automatically selected skin safety limit of the variable radiation parameter; and
      said actuator is configured to further permit changing the variable radiation parameter manually, but not beyond the automatically selected skin safety limit.

2. The skin treatment apparatus according to claim 1, wherein the automatically selected skin safety limit is a maximum power.

3. The skin treatment apparatus according to claim 2, wherein said actuator enables sequential actuation by a user that selects a power progressively lower than the maximum power.

4. The skin treatment apparatus according to claim 3, wherein once the lowest power has been selected, further actuation of said actuator resets said power to the maximum power.

5. The skin treatment apparatus according to claim 1, wherein said control unit comprises a first memory for storing said sensed skin parameter.

6. The skin treatment apparatus according to claim 5, wherein said base unit includes a second memory and said sensed skin parameter is downloadable from said control unit to said first memory when said control unit is docked to the base unit.

7. The skin treatment apparatus according to claim 1, wherein said control unit further comprises a plurality of indicators for indicating a magnitude of the parameter of the radiation to be generated by said radiation source.

8. The skin treatment apparatus according to claim 1, further comprising a timing circuit for preventing generation of radiation from said radiation source when said radiation source is not activated within a pre-determined time following the docking of said control unit to said base unit.

* * * * *